(12) United States Patent
Murphy

(10) Patent No.: US 9,427,254 B2
(45) Date of Patent: Aug. 30, 2016

(54) APPARATUS FOR USE IN A SURGICAL PROCEDURE

(71) Applicant: Kieran P. Murphy, Baltimore, MD (US)

(72) Inventor: Kieran P. Murphy, Baltimore, MD (US)

(73) Assignee: KIERAN MURPHY LLC, Towson, MD (US)

( * ) Notice: Subject to any disclaimer, the term of this patent is extended or adjusted under 35 U.S.C. 154(b) by 139 days.

(21) Appl. No.: 13/858,609

(22) Filed: Apr. 8, 2013

(65) Prior Publication Data

US 2013/0226210 A1    Aug. 29, 2013

Related U.S. Application Data

(60) Continuation of application No. 13/190,830, filed on Jul. 26, 2011, now abandoned, which is a division of application No. 11/081,494, filed on Mar. 17, 2005, now abandoned, which is a division of application No. 10/373,835, filed on Feb. 27, 2003, now abandoned.

(60) Provisional application No. 60/366,530, filed on Mar. 25, 2002, provisional application No. 60/366,529, filed on Mar. 25, 2002.

(51) Int. Cl.
*A61B 5/00* (2006.01)
*A61B 17/34* (2006.01)
*A61L 31/18* (2006.01)
*A61B 6/00* (2006.01)
*A61B 6/03* (2006.01)
*A61B 10/02* (2006.01)

(52) U.S. Cl.
CPC ......... *A61B 17/3403* (2013.01); *A61B 6/4423* (2013.01); *A61L 31/18* (2013.01); *A61B 6/03* (2013.01); *A61B 10/0233* (2013.01); *Y10T 428/24273* (2015.01)

(58) Field of Classification Search
CPC .......... A61B 17/8819; A61B 17/3421; A61B 17/3401; A61B 2017/00469; A61B 18/1477
USPC .................................................. 600/562–567
See application file for complete search history.

(56) References Cited

U.S. PATENT DOCUMENTS 3,721,997 A    3/1973  Mundt
3,984,696 A   10/1976  Collica et al.
(Continued)

FOREIGN PATENT DOCUMENTS

CA         2471958       6/2003
DE        003405837     10/1985
(Continued)

OTHER PUBLICATIONS

Office Action dated Feb. 28, 2012 for U.S. Appl. No. 11/081,494.
(Continued)

*Primary Examiner* — Max Hindenburg
(74) *Attorney, Agent, or Firm* — Perry + Currier Inc.

(57) ABSTRACT

An embodiment of the present invention provides a kit of parts for use in a surgical procedure performed under image guidance, and particularly under real time image guidance. The kit includes a sterilized drape for use with the chosen imaging machine and which can be used to provide a sterile operating environment when the procedure is performed under the imaging beam. The kit also includes a needle holder that can keep the surgeon's hand away from the imaging beam. The needle holder is operable to hold a needle that is made from a material suitable for piercing tissue, but also substantially preserves the appearance of the needle when it is viewed under the imaging beam.

12 Claims, 7 Drawing Sheets

(56) References Cited

U.S. PATENT DOCUMENTS

| | | | |
|---|---|---|---|
| 4,062,518 | A | 12/1977 | Stivender et al. |
| 4,258,722 | A * | 3/1981 | Sessions ............ A61B 10/025 600/566 |
| 4,391,276 | A | 7/1983 | Lazarus et al. |
| 4,465,069 | A | 8/1984 | Barbier et al. |
| 4,533,356 | A | 8/1985 | Bengmark et al. |
| 4,610,671 | A * | 9/1986 | Luther .................... 604/168.01 |
| 4,655,226 | A * | 4/1987 | Lee ................ 600/567 |
| 4,686,962 | A | 8/1987 | Haber |
| 4,732,933 | A | 3/1988 | Maeda et al. |
| 4,733,665 | A | 3/1988 | Palmaz |
| 4,739,762 | A | 4/1988 | Palmaz |
| 4,776,337 | A | 10/1988 | Palmaz |
| 4,795,458 | A | 1/1989 | Regan |
| 4,940,458 | A | 7/1990 | Cohn |
| 4,994,066 | A | 2/1991 | Voss |
| 5,037,427 | A | 8/1991 | Harada et al. |
| 5,058,577 | A * | 10/1991 | Six .......................... 128/200.26 |
| 5,064,435 | A | 11/1991 | Porter |
| 5,067,957 | A | 11/1991 | Jervis |
| 5,084,022 | A | 1/1992 | Claude |
| 5,102,417 | A | 4/1992 | Palmaz |
| 5,147,308 | A * | 9/1992 | Singer .......................... 604/117 |
| 5,169,386 | A | 12/1992 | Becker et al. |
| 5,211,165 | A | 5/1993 | Dumoulin et al. |
| 5,242,455 | A | 9/1993 | Skeens et al. |
| 5,250,035 | A * | 10/1993 | Smith et al. ............. 604/168.01 |
| 5,292,339 | A | 3/1994 | Stephens et al. ................ 607/15 |
| 5,311,883 | A | 5/1994 | Sherman |
| 5,335,663 | A | 8/1994 | Oakley et al. |
| 5,403,341 | A | 4/1995 | Solar |
| 5,444,871 | A | 8/1995 | Lopez |
| 5,482,043 | A | 1/1996 | Zulauf |
| 5,492,130 | A * | 2/1996 | Chiou .......................... 600/566 |
| 5,499,418 | A | 3/1996 | Tan et al. |
| 5,522,881 | A | 6/1996 | Lentz |
| 5,522,882 | A | 6/1996 | Gaterud et al. |
| 5,531,737 | A | 7/1996 | Schade |
| 5,545,150 | A | 8/1996 | Danks et al. |
| 5,546,961 | A | 8/1996 | Harrison |
| 5,549,439 | A | 8/1996 | Ploem |
| 5,549,635 | A | 8/1996 | Solar |
| 5,556,414 | A | 9/1996 | Turi |
| 5,562,726 | A | 10/1996 | Chuter |
| 5,575,798 | A | 11/1996 | Koutrouvelis |
| 5,590,655 | A | 1/1997 | Hussman |
| 5,591,195 | A | 1/1997 | Taheri et al. |
| 5,592,952 | A | 1/1997 | Bohn |
| 5,607,467 | A | 3/1997 | Froix |
| 5,609,629 | A | 3/1997 | Fearnot et al. |
| 5,638,819 | A | 6/1997 | Manwarring et al. |
| 5,676,159 | A | 10/1997 | Navis |
| 5,693,015 | A | 12/1997 | Walker et al. |
| 5,702,682 | A | 12/1997 | Thompson |
| 5,725,572 | A | 3/1998 | Lam et al. |
| 5,735,892 | A | 4/1998 | Meyers et al. |
| 5,741,333 | A | 4/1998 | Frid |
| 5,746,765 | A | 5/1998 | Kleshinski et al. |
| 5,772,669 | A | 6/1998 | Vrba |
| 5,782,764 | A * | 7/1998 | Werne .......................... 600/411 |
| 5,788,626 | A | 8/1998 | Thompson |
| 5,788,707 | A | 8/1998 | Del Toro et al. |
| 5,797,952 | A | 8/1998 | Klein |
| 5,800,517 | A | 9/1998 | Anderson et al. |
| 5,810,870 | A | 9/1998 | Myers et al. |
| 5,824,045 | A | 10/1998 | Alt |
| 5,857,997 | A | 1/1999 | Cimino et al. |
| 5,861,033 | A | 1/1999 | Martakos et al. |
| 5,876,448 | A | 3/1999 | Thompson et al. |
| 5,892,238 | A | 4/1999 | Huttner et al. |
| 5,899,935 | A | 5/1999 | Ding |
| 5,902,254 | A | 5/1999 | Magram |
| 5,906,618 | A | 5/1999 | Larson, III |
| 5,908,405 | A | 6/1999 | Imran |
| 5,922,020 | A | 7/1999 | Klein et al. |
| 5,925,074 | A | 7/1999 | Gingras et al. |
| 5,957,974 | A | 9/1999 | Thompson et al. |
| 5,980,565 | A | 11/1999 | Jayaraman et al. |
| 5,989,280 | A | 11/1999 | Euteneuer et al. |
| 6,010,529 | A | 1/2000 | Herweck et al. |
| 6,059,759 | A | 5/2000 | Mottola et al. |
| 6,086,610 | A | 7/2000 | Duerig |
| 6,120,536 | A | 9/2000 | Ding et al. |
| 6,126,654 | A | 10/2000 | Giba et al. |
| 6,146,418 | A | 11/2000 | Berman |
| 6,179,878 | B1 | 1/2001 | Duerig et al. |
| 6,236,875 | B1 | 5/2001 | Bucholz et al. |
| 6,270,523 | B1 | 8/2001 | Herweck et al. |
| 6,283,125 | B1 | 9/2001 | McNeirney et al. |
| 6,285,902 | B1 | 9/2001 | Kienzle, III et al. |
| 6,298,110 | B1 | 10/2001 | Ning |
| 6,315,791 | B1 | 11/2001 | Gingras |
| 6,325,538 | B1 | 12/2001 | Heesch |
| 6,352,561 | B1 | 3/2002 | Leopold et al. |
| 6,355,058 | B1 | 3/2002 | Pacetti et al. |
| 6,374,937 | B1 | 4/2002 | Galando et al. |
| 6,379,302 | B1 | 4/2002 | Kessman et al. |
| 6,400,979 | B1 | 6/2002 | Stoianovici et al. |
| 6,412,851 | B1 | 7/2002 | Burks et al. |
| 6,423,089 | B1 | 7/2002 | Gingras et al. |
| 6,428,557 | B1 | 8/2002 | Hilaire |
| 6,447,540 | B1 | 9/2002 | Fontaine et al. |
| 6,453,185 | B1 | 9/2002 | O'Keefe |
| 6,456,684 | B1 | 9/2002 | Mun et al. |
| 6,475,234 | B1 | 11/2002 | Richter |
| 6,475,235 | B1 | 11/2002 | Jayaraman |
| 6,481,888 | B1 | 11/2002 | Morgan |
| 6,490,467 | B1 | 12/2002 | Bucholz et al. |
| 6,490,475 | B1 | 12/2002 | Seeley et al. |
| 6,511,471 | B2 | 1/2003 | Roseman et al. |
| 6,530,933 | B1 | 3/2003 | Yeung et al. |
| 6,533,806 | B1 | 3/2003 | Sullivan et al. |
| 6,544,041 | B1 | 4/2003 | Damadian |
| 6,578,219 | B1 | 6/2003 | Gabel et al. |
| 6,585,677 | B2 | 7/2003 | Cowan, Jr. et al. |
| 6,585,755 | B2 | 7/2003 | Jackson et al. |
| 6,629,992 | B2 | 10/2003 | Bigus et al. |
| 6,635,064 | B2 | 10/2003 | U et al. |
| 6,656,213 | B2 | 12/2003 | Solem |
| 6,679,886 | B2 | 1/2004 | Weikel et al. |
| 6,689,125 | B1 | 2/2004 | Keith et al. |
| 6,716,238 | B2 | 4/2004 | Elliot |
| 6,734,937 | B2 | 5/2004 | Nakasogi et al. |
| 6,740,113 | B2 | 5/2004 | Vrba |
| 6,857,778 | B2 | 2/2005 | Mun et al. |
| 6,932,787 | B2 | 8/2005 | Cowan et al. |
| 6,961,606 | B2 | 11/2005 | DeSilets et al. |
| 7,391,042 | B2 | 6/2008 | Goldstein |
| 8,317,727 | B2 | 11/2012 | Peliks |
| 8,622,924 | B2 | 1/2014 | Speeg et al. |
| 8,628,475 | B2 | 1/2014 | Wang |
| 9,149,293 | B2 | 10/2015 | Hardert et al. |
| 2001/0041928 | A1 | 11/2001 | Pavcnik et al. |
| 2002/0002383 | A1 | 1/2002 | Sepetka et al. |
| 2002/0022825 | A1 | 2/2002 | Saitou et al. |
| 2002/0040239 | A1 | 4/2002 | Murayama et al. |
| 2002/0052640 | A1 | 5/2002 | Bigus et al. |
| 2002/0077540 | A1 | 6/2002 | Kienzle |
| 2002/0183610 | A1 | 12/2002 | Foley et al. |
| 2002/0183763 | A1 | 12/2002 | Callol et al. |
| 2002/0196906 | A1 | 12/2002 | Mun et al. |
| 2003/0004563 | A1 | 1/2003 | Jackson et al. |
| 2004/0073286 | A1 | 4/2004 | Armstrong et al. |
| 2004/0082905 | A1 | 4/2004 | Solar et al. |
| 2004/0148000 | A1 | 7/2004 | Bilge |
| 2004/0176682 | A1 | 9/2004 | Murphy |
| 2004/0176833 | A1 | 9/2004 | Pavcnik et al. |
| 2004/0176835 | A1 | 9/2004 | Vrba |
| 2004/0241094 | A1 | 12/2004 | Chung et al. |

(56) References Cited

U.S. PATENT DOCUMENTS

| | | | |
|---|---|---|---|
| 2006/0104999 | A1 | 5/2006 | Chung et al. |
| 2006/0134144 | A1 | 6/2006 | Chung et al. |
| 2008/0182282 | A1 | 7/2008 | Markman et al. |

FOREIGN PATENT DOCUMENTS

| | | |
|---|---|---|
| DE | 3918736 | 12/1990 |
| DE | 3918736 A1 | 12/1990 |
| EP | 0578998 A1 | 1/1994 |
| EP | 0 797 988 A2 | 10/1997 |
| EP | 0578988 | 10/1997 |
| EP | 0578998 | 10/1997 |
| EP | 0797988 | 10/1997 |
| EP | 0809998 | 12/1997 |
| EP | 0809998 A2 | 12/1997 |
| EP | 0872220 | 10/1998 |
| EP | 947204 | 10/1999 |
| EP | 947204 A2 | 10/1999 |
| EP | 0947204 | 12/2000 |
| EP | 1 155 689 A2 | 11/2001 |
| EP | 1155689 | 11/2001 |
| EP | 1362603 | 11/2003 |
| WO | 98/26731 A2 | 6/1998 |
| WO | 9826731 | 6/1998 |
| WO | 00/24338 A1 | 5/2000 |
| WO | 0024338 | 5/2000 |
| WO | 00/40159 | 7/2000 |
| WO | WO 0040159 | 7/2000 |
| WO | 03094798 | 11/2003 |

OTHER PUBLICATIONS

Choquette et al. Direct Selenium X-Ray Detector for Fluoroscopy, R&F, and Radiography, 2000, In Medical Imaging 2000: Physics of Medical Imaging, Proceedings of SPIE vol. 3977, pp. 128-136.

Office Action for U.S. Appl. No. 13/047,226 dated Apr. 13, 2011.

Munshi I, Lathrop D, Madsen Jr, Frim DM; "Intraventricular Pressure Dynamics in Patients with Ventriculopleural Shunts: A Telemetric Study"; Pediatric Neurosurgery; 1998; vol. 28; pp. 67-69.

Jose M. Montes, MD; John H. Wong, MD; Pierre B. Fayad, MD; Issam A. Awad, MD; Stereotactic Computed Tomographic-Guided Aspiration and Thrombolysis of Intracerebral Hematoma Stroke Apr. 2000; vol. 31: pp. 834-840.

Neal J. Naff, MD; Juan R. Carhuapoma, MD; Michael A. Williams, MD; Anish Bhardwaj, MD; John A. Ulaowski, MD, PhD; Joshua Bederson, MD; Ross Bullok, MD; Eric Schmutzhard, MD; Bettina Pfausler, MD; Penelope M. Keyl, PhD; Stanley Tuhrim, MD; Daniel F. Hanley, MD; "Treatment of Intraventricular Hemorrhage With Urokinase Effects on 30-Day Survival"; Stroke, Apr. 2000; vol. 31 pp. 841-847.

Miyake, Hiroji MD; Ohta, Tomio MD; Kajimoto, Yoshinaga MD; Matsukawa, Masanori MD; "A New Ventriculoperitoneal Shunt with a Telemetric Intracranial Pressure Sensor: Clinical Experience in 94 Patients with Hydrocephalus"; Neurosurgery. 40(5): 931-935, May 1997.

Dr. Hans-Ulrich Laasch et al., "Revision Notes for the FRCR Part 1", The Society of Radiologists in Training, 1999 (60 pages).

A.C. Kak Malcolm Slaney, "Principles of Computerized Tomographic Imaging", Chapter 4 (Measurement of Projection Data— The Nondiffracting Case), pp. 113-134, IEEE, 1988.

Anthony R. Kovscek et al., "Stanford University Petroleum Research Institute Preliminary Twenty-Fourth Annual Report", Apr. 19-21, 2001 (68 pages).

Google's Cache of http://www.bicetre.neuroradio.net/french/journal/menu.htm. at http://www.google.com/search?q=cacheU20QRBv7hYC; www.bicetre.neuroradio.net/french/journal/menu.htm=MCTA+angiography&hi=en&ie+UTF8, Index MARS 2002 (5 pages).

Gailloud P. Hillis, A., Perler, B.; and Murphy, K.J. "Vertebrobasilar Stroke as a Late Complication of a Blalock-Taussig Shunt", Wiley-Liss, Inc., 2002, pp. 231-234.

Google's Cache of http://www.google.ca/search?q=%houndsfield+unit%22&ie=UTF-8&oe=UTF8&hl=en&meta=, Mar. 21, 2003 (60 pages).

Dolmach, Bart, MD., et al., "Patency and Tissue Response Related to Two Types of Polytetrafluroethylene-Covered Stens in the dog," Journal of Vascular and Interventional Radiology, vol. 7 No. 5 Sep.-Oct. 1996, pp. 642-649.

Michael Strotzer, MD., et al. "Appearance of Vascular Stents in Computed Tomographic Angiography: In Vitro Examination of 14 Different Stent Types," Investigative Radiology, vol. 36: (11) pp. 652-658, Nov. 2001.

Stefan Hahnel, et al., "Small-Vessel Stents for Intracranial Angioplasty: In Vitro Comparison of Different Stent Designs and Sizes by Using CT Angiography," AJNR AM J Neuroradiol 24:1512-1516, Sep. 2003.

David Maintz et al., "Revealing in_Stent Stenoses of the Iliac Arteries: Comparison of Multidetector CT with MR Angiography and Digital Radiographic Angiography in a Phantom Model," AJR:179, p. 1319-1322, Nov. 2002.

Henry Brem, et al. "Polymer-Based Drug Delivery to the Brain," Science & Medicine, Inc., vol. 3, No. 4, p. 1-11, Jul./Aug. 1996.

Stephen Schroeder, et al. "Influence of Heart Rate on Vessel Visibility in Noninvasive Coronary Angiography Using New Multislice Computed Tomography Experience in 94 Patients," Journal of Clinical Imaging 26 (2002), pp. 106-107.

Paul P. Wang et al., "Local Drug Delivery to the Brain," Advanced Drug Delivery Review 54 (2002) pp. 987-1013.

Antezanna DF, et al., "High-dose Ibuprofen for reduction of striatal infarets during middle cerebral artery occlusion in rats," http://www.ncbi.nlm.nih.gov:80/entrez/query.fcgi?cmd=PubMed&list-uids+12691413&dopt=Abstract; last visited on Oct. 1, 2003 (2 pages).

Patrik Gabikian, MD et al., "Stroke: Prevention of Experimental Cerebral Vasospasm by Intracranial Delivery of Nitric Oxide Donor From Controlled-Release Polymer," http://stroke.ahajournals.org/cgi/content/full/33/11/12681, last visited on Oct. 1, 2003 (11 pages).

Travis S. Tierney, et al., "Prevention and Reversal of Experimental Posthemorrhagic Vasospasm by the Periadventitial Administration of Nitric Oxide From a Controlled-release Polymer," http://www.neurosurgery-online/fulltext/4904/0945/NURO49040945-doc.html, vol. 49 No. 4, Oct. 2001 (11 pages).

Rafael J. Tamargo, et al. "The Intracerebral Administration of Phenytoin Using Controlled-Release Polymers Reduces Experimental Seizures in Rats," Epillepsy Research 48, p. 145-155 (2002).

J. Golzarian, Imaging After Endovascular Repair of Abdominal Aortic Aneurysm, Abdominal Imaging 28, p. 236-243 (2003).

Jens Rodenwaldt, Multislice Computed Tomography of the Coronary Arteries, Eur Radiol (2003) 13:748-757, Jan. 2003.

Stefanie Weigel et al., "Thoracic Aortic Stent Graft: Comparison of Contrast-Enhanced MR Angiography and CT Angiography in the Follow-Up: Initial Results," Eur Radiol (2003) 13: 1628-1634, Feb. 2003.

Quoc-Anh Thai, BA et al., "Inhibition of Experimental Vasospasm in Rats with the Periadventital Administration of Ibprofen Using Controlled-Release Polymers," published by American Heart Association, pp. 140-147 Jan. 1999.

Langer R. Brem et al., "Biocompatibility of Polymeric Delivery System for Macromolecules," http://www.ncbi,nlm.nlh.gov:80/entrez/query.fcgi?cmd=Retrieve&db=PubMedlist-uids+2772427&dopt=Abstract, last visited on Oct. 3, 2003 (1 page).

Seung-Jung Park, MD., et al., "A Paclitaxel-Eluting Stent for the Prevention of Coronary Restenosis," The New England Journal of Medicine, vol. 348:1537-1545 No. 16, Apr. 17, 2003.

Allan W. Heldman, MD et al., Paclitaxel Stent Coating Inhibits Neointimal Hyperplasia at 4 weeks in Porcine Model of Coronary Restenosis, published by the American Heart Association, Inc., pp. 2289-2295, May 2001.

Jonette Foy, Phd., "Drug-Eluting Stents: Pre-Clinical Standards & Recommended Studied." FDA/SIR Device Forum Meeting, Nov. 2002.

Drake et al. The Shunt Book, Copyright 1995 Blackwell Science in Massachusettes.

(56) References Cited

OTHER PUBLICATIONS

Kopp A F, Ohnsesorge B, Flohr T, Georg C. Schroeder S. Kuttner A, Martensen, J. Claussen CD Cardiac multidetector-row CT; First Clinical Results of retrospectively ECG-gated spiral with optimized temporal and spatial resolution, Rofo Fortschr Geb Rotgenstr Neuen Bildgeb Verfahr May 2000 172(5) 429-35.
Ohnessorge B, Flohr T. Becker C, Knex A, Knopp A F Fukada K Reiser M F Cardiac Imaging with rapid, retrospective ECG Synchronized multilevel spiral CT Radiologe, Feb. 200; 40 (2) 111-7.
Achenbach S. Moshage W, Ropers D, Nossen J Bachmann K, Non-invasive Coronary Angiography with Electron Beam Tomography: Methods and Clinical Evaluation in Post-PTCA Follow-up Z Kardiol, Feb. 1997; 86(2) 121-30.
Becker C R, Schoepf U J, Reiser M F., Methods for Quantification of Coronary Artery Calsifications with Electrogram Beam and Conventional CT and Pushing the Spiral CT Envelope; New Cardiac Applications, Int J. Cardiovasc Imaging Imaging, Jun. 17, 2001; (3): 203-11.
Kopp A F, Schroeder S, Kuettner A, Baumbach A Georg C, Kuzo R, Heuschmid M, Ohnesorge B, Karsch K R, Claussen C D, Noninvasive Coronary Angiography with High Resolution Multidetector-Row Computed Tomography Results in 102 Patients, Eur Heart J., Nov. 23, 2002; (21); 1714-25.
Achenbach S, Ulzheimer S, Baum U, Kachelriess M, Ropers D, Giesler T, Bautz W. Daniel W G, Kalender W A, Moshage W, Noninvasive Coronary Angiography by Retrospectively ECG-Gated Multislice Spiral CT, Circulation, Dec. 5, 2000: 102(23):2823-8.
Knez A, Becker A, Becker C, Leber A Boekstegers P, Reiser M, Steinbeck G., Detection of Coronary Calcinosis with Multislice Spiral Computerization Tomography: An Alternative to Electron Bean Tomography, Z. Kardiol, Aug. 2002:01 (8): 642-9.
Mahnken A H, Sinha A M, Wildberger J E, Krombach G A , Schmitz-Rode T, Gunther R W , The Influence of Motion Artifacts Conditioned by Reconstruction, on the Coronary Clacium Score in Multislice Spiral CT, Rofo Fortschr Geb Rontgenstr Neuen Bildgeb Verahr, Oct. 2001; 173(10): 888-92.
Moses et al., Sirlumus Eluting Stents Versus Standard Stents in Patients with Stenosis of the Coronary Artery, New England Journal of Medicine, p. 1315-1323, Oct. 2, 2003 vol. 349.
Fossa Medical Welcome to Fossa Medical.com @ URL <http://www.fossamedical.com/news.htm. from Sep. 9, 2005 (retrieved on Sep. 18, 2008).
Stone Sweeper (r) Kidney Stone Removal Device: The Clear Path to Ureteral Patency—Insertion Instructions, at URL<http://www.fossamedical.com/pdfs/sweepersurgicaltechnique.pdf>, 2004 (retrived on Sep. 18, 2008).
H. Brem, et al. Biocompatibility of Biodegradable controlled released polymer in the rabbit brain, http://www.ncbi.nlm.nih.gov:80/entrz/query.fcgi?cmd=Retrieve&db=PubMed&list_uids=2772427&dopt=Abstract, last visited on Oct. 3, 2003 (1 page).
Lee, Y., et al, Synthesis of 188 Re-labelled long chain alkyl diaminedithiol for therapy of liver cancer, Nuclear Medicine Communications, Mar. 2002—vol. 23, Issue 3, pp. 237-242.
Canadian Office Action dated Mar. 9, 2011 for Application No. 2,455,439.
Jose M. Montes, MD; John H. Wong, MD; Pierre B. Fayad, MD Issam A. Awad, MD; "Stereotactic Computed Tomographic—Guided Aspiration and Thrombolysis of Intracerebral Hematonna" Stroke. Apr. 2000; vol. 31: pp. 834-840.
Neal J. Naff, MD; Juan R. Carhuapoma, MD; Michael A. Williams, MD; Anish Bhardwaj, MD; John A. Ulatowski, MD, PhD; Joshua Bederson, MD; Ross Bullock, MD; Erich Schmutzhard, MD; Bettina Pfausler, MD; Penelope M. Keyl, PhD; Stanley Tuhrim, MD Daniel F. Hanley, MD ; "Treatment of Intraventricular Hemorrhage With Urokinase Effects on 30-Day Survival"; Stroke. Apr. 2000; vol. 31: pp. 841-847.
Miyake, Hiroji MD; Ohta, Tomio MD; Kajimoto, Yoshinaga MD; Matsukawa, Masanori MD; "A New Ventriculoperitoneal Shunt with a Telemetric Intracranial Pressure Sensor: Clinical Experience in 94 Patients with Hydrocephalus"; Neurosurgery. 40(5):931-935, May 1997.
Dr. Hans-Ulrich Laasch et ai', "Revision Notes for the FRCR Part 1", The Society of Radiologists in Training, 1999 (60 pages).
A.C. Kak and Malcolm Slaney, "Principles of Computerized Tomographic Imaging", Chapter 4 (Measurement of Projection Data—The Nondiffracting Case), pp. 113-134, IEEE, 1988 (22 pages).
Google's Cache of http://www.bicetre.neuroradio.net/frenchljournal/ menu .htm. at http://www.google.com/search?q=cacheU20QRBv7hYC; www.bicetre.neuroradio.net/french/journal/menu.htm+MCTA+angiography&hl=en&ie+UTF8, Index MARS 2002 (5 pages).
Gailoud, P.; Hillis, A.; Perler, B.; and Murphy, K.J. "Vertebrobasilar Stroke as a Late Complication of a Blalock-Taussig Shunt", Wiley-Liss, Inc., 2002, pp. 231-234 (4 pages).
Google's Cache of http://ww.google.ca/search?q=%houndsfield+unit% 22&ie=UTF-8&oe=UTF8&hl=en&meta=, Mar. 21, 2003 (60 pages).
Dolmatch, Bart. M.D., et al., "Patency and Tissue Response Related to Two Types of Polytetrafluoroethylene-Covered Stents in the Dog," Journal of Vascular and Interventional Radiology. vol. 7, No. 5, Sep.-Oct. 1996, pp. 642-649 (9 pages).
Michael Strotzer, MD, et al., "Appearance of Vascular Stents in Computed Tomographic Angiography: In Vitro Examination of 14 Different Stent Types," Investigative Radiology, vol. 36: (11) p. 652-658, Nov. 2001, (6 pages).
Stefan Hahnel, el al., "Small-Vessel Stents for Intracranial Angioplasty: In Vitro Comparison of Different Stent Designs and Sizes by Using CT Angiography," AJNR Am J Neuroradiol 24:1512-1516, Sep. 2003 (6 pages).
David Maintz, et al., "Revealing In-Stent Stenoses of the Ilac Arteries: Comparison of Multidelector CT with MR Angiography and Digital Radiographic Angiography in a Phantom Model," AJR:179, p. 1319-1322, Nov. 2002 (4 pages).
Henry Brem, et al., "Polymer-Based Drug Delivery to the Brain," Science & Medicine, Inc., vol. 3, No. 4, p. 1-11, Jul./Aug. 1996 (11 pages).
Stephen Schroeder, et al., "Influence of Heart Rate on Vessel Visibilty in Noninvasive Coronary Angiography Using New Multislice Computed Tomography Expenence in 94 Patients," Journal of Clinical Imaging 26 (2002), p. 106-107, 2002 (2 pages).
Paul P. Wang. et al., "Local Drug Delivery to the Brain," Advanced Drug Delivery Review 54 (2002), p. 987-1013, (27 pages).
Antezanna DF. et al., "High-dose Ibuprofen for reduction of striatal infarets during middle cerebral artery occlusion in rats," http://www.ncbi.nlm.nih.gov:80/entrez/query .fcgi?cmd=PubMed&list_uids+12691413&dopt=Abstract; last visited on Oct. 1, 2003 (2 pages).
Patrik Gabikian, MD. et al., "Stroke: Prevention of Experimental Cerebral Vasospasm by Intracranial Delivery of a Nitric Oxide Donor From a Controlled-Release Polymer," http://stroke.ahajournals.org/cgi/content/full/33/11/2681, last visited on 10101/2003 (11 pages).
Travis S. Tiemey, et al., "Prevention and Reversal of Expenmental Posthemorrhagic Vasospasm by the Periadventital Administration of Nitric Oxide From a Controlled-release Polymer," http:/www.neurosurgery-online/fulltext/4904/0945/NUR049040945_doc.html, vol. 49, No. 4. Oct. 2001 (11 pages).
Rafael J. Tamargo, et al.. "The Intracerebral Administration of Phenytoin Using Controlled-Release Polymers Reduces Experimental Seizures in Rats," Epilepsy Research 48, p. 145-155; 2002 (11 pages).
J. Golzarian, "Imaging After Endovascular Repair of Abdominal Aortic Aneurysm." Abdominal Imaging 28, p. 236-243, 2003 (8 pages).
Jens Rodenwaldt, "Multislice Computed Tomography of the Coronary Arteries," Eur Radiol (2003) 13:748-757, Jan. 2003 (10 pages).
Stefanie Weigel, et al.. "Thoracic Aortic Stent Graft: Comparison of Contrast-Enhanced MR Angiography and CT Angiopgraphy in the Follow-Up: Initial Results," Eur Radiol (2003) 13:1628-1634, Feb. 2003 (7 pages).

(56) References Cited

OTHER PUBLICATIONS

Quoc-Anh Thai, BA, et al., "Inhibition of Experimental Vasospasm in Rats with the Periadventital Administration of Ibuprofen Using Controlled-Release Polymers," published by Amencan Heart Association, p. 140-147, Jan. 1999 (8 pages).

Langer R. Brem, et al., "Biocompatibilty of Polymeric delivery systems for macromolecules," http://www.ncbi.nlm.nih.gov;80/entrez/query.fcgi?cmd=Retrieve&db=PubMed&list_uids=7348718&dopt=Abstract, last visited on Oct. 31, 2003 (1 page).

H. Brem, et al., "Biocompatibilty of a biodegradable, controlled-release polymer in the rabbit brain," http://www.ncbi .nlm.nih.gov:80/entrez/query .fcgi?cmd=Retrieve&db=PubMed&list_uids=2772427&dopt=Abstract, last visited on Oct. 3, 2003 (1 page).

Seung-Jung Park, M.D., et al., "A Paclitaxel-Eluting Stent for the Prevention of Coronary Restenosis," The New England Journal of Medicine, vol. 348:1537-1545, No. 16, Apr. 17, 2003, (3 pages).

Allan W. Heldman, MD, et al., "Paclitaxel Stent Coating Inhibits Neointimal Hyperplasia at 4 weeks in a Porcine Model of Coronary Restenosis," published by Amencan Heart Association, Inc., p. 2289-2295, May 2001 (7 pages).

Jonette Foy, Ph.D., "Drug-Eluting Stents: Pre-Clinical Standards & Recommended Studies," FDA/SIR Device Forum Meeting, Nov. 2002 (7 pages).

Drake et al., The Shunt Book, Copyrgt. 1995 Blackwell Science Inc. Massachusetts.

Kopp A F, Ohnesorge B, Flohr T, Georg C, Schroeder S, Kuttner A, Martensen,J, Claussen C D., Cardiac multidetector-row CT: first clinical results of retrospectively ECG-gated spiral with optimized temporal and spatial resolution, Rofo Fortschr Geb Rontgenstr Neuen Bildgeb Verfahr. May 2000; 172(5):429-35.

Ohnesorge B, Flohr T, Becker C, Knex A, Kopp A F, Fukuda K. Reiser M F., Cardiac imaging with rapid, retrospective ECG synchronized multilevel spiral CT Radiologe, Feb. 2000:40(2): 111-7.

Achenbach S, Moshage W, Ropers D, Nossen J, Bachmann K, Non-invasive coronary angiography with electron beam tomography: methods and clinical evaluation in post-PTCA follow-up Z Kardiol., Feb. 1997; 86(2):121-30.

Becker C R, Schoepf U J, Reiser M F., Methods for quantification of coronary artery calcificatins with electron beam and conventional CT and pushing the spiral CT envelope: new cardiac applications. Int J Cardiovasc Imaging, Jun. 17, 2001;(3):203-11.

Kopp A F, Schroeder S, Kuettner A, Baumbach A, Georg C, Kuzo R, Heuschmid M, Ohnesorge B, Karsch K R, Claussen C D, Non-invasive coronary angiography with high resolution multidetector-row computed tomography. Results in 102 patients. Eur Heart J. Nov. 23, 2002;(21): 1714-25.

Achenbach S, Ulzheimer S,Baum U, Kachelriess M. Ropers D, Giesler T. Bautz W, Daniel W G, Kalender W A, Moshage W, Noninvasive coronary angiography by retrospectively ECG-gated multislice spiral CT. Circulation. Dec. 5, 2000:102(23):2823-8.

Knez A, Becker A, Becker C, Leber A, Boekstegers P, Reiser M, Steinbeck G,, Detection of coronary calcinosis with multislice spiral computerized tomography: an alternative to electron beam tomography Z Kardiol. Aug. 2002:91 (8):642-9.

Mahnken A H, Sinha A M, Wildberger J E, Krombach G A, Schmitz-Rode T, Gunther R W, The influence of motion artifacts conditioned by reconstruction, on the coronary calcium score in multislice spiral CT, Rofo Fortschr Geb Rontgenstr Neuen Bildgeb Verfahr, Oct. 2001;173(10):888-92.

Moses et al., Sirilumus eluting stents versus stanrd stents in patients with stenosis of the coronary artery, New England Journal of Medicine, p. 1315-1323 Oct. 2, 2003 vol. 349, No. 14.

John Summerscales, Non-destructive testing of fibre-reinforced plastics composites, vol. 2; Elsevier Science Publishers Ltd, 1990; p. 208.

Choquette et al., Direct selenium x-ray detector for fluoroscopy, R&F, and radiography, 2000, In Medical Imaging 2000: Physics of Medical Imaging, Proceedings of SPIE vol. 3977, pp. 128-136.

U.S. Office Action mailed Jan. 21, 2016 for U.S. Appl. No. 14/516,218.

U.S. Office Action mailed Dec. 10, 2015 for U.S. Appl. No. 14/709,220.

* cited by examiner

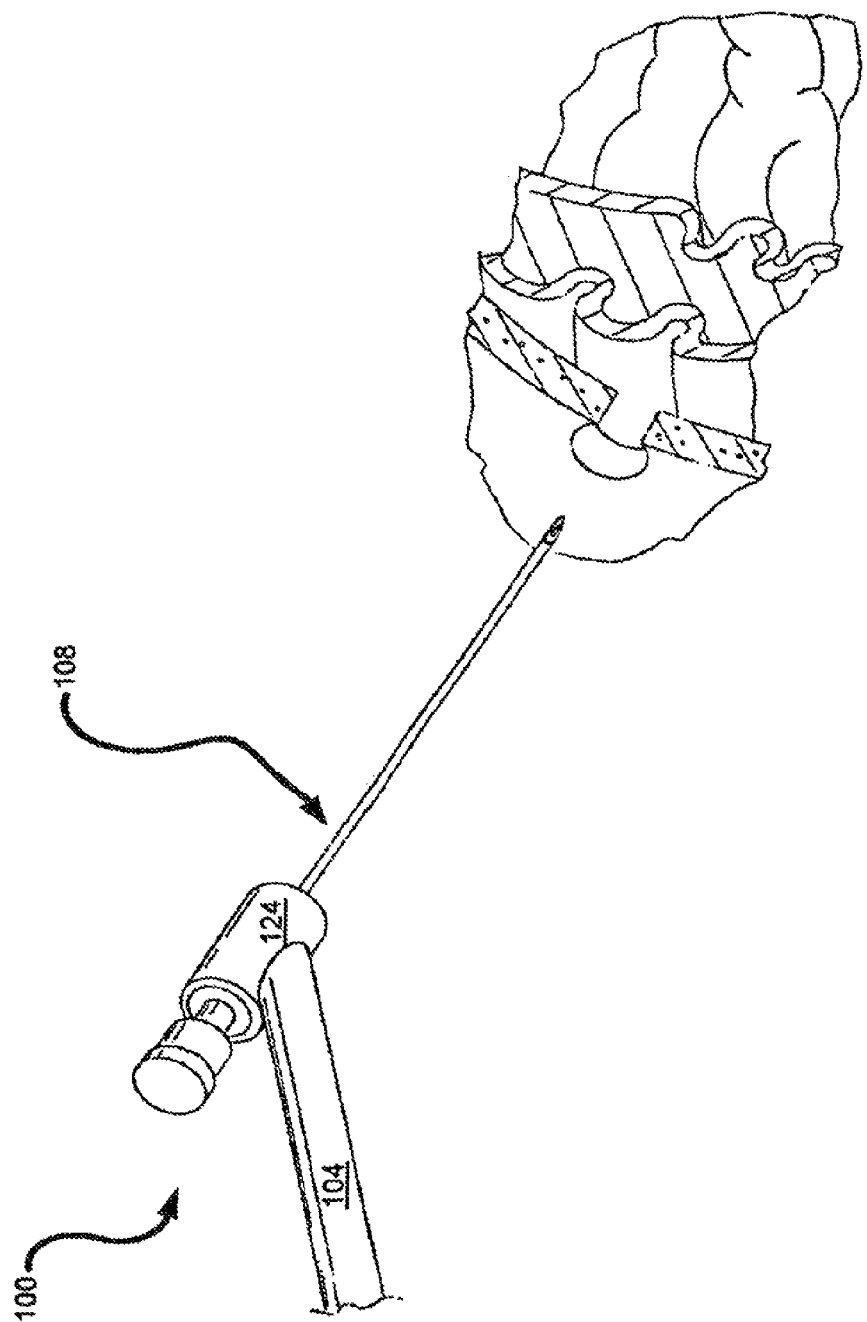

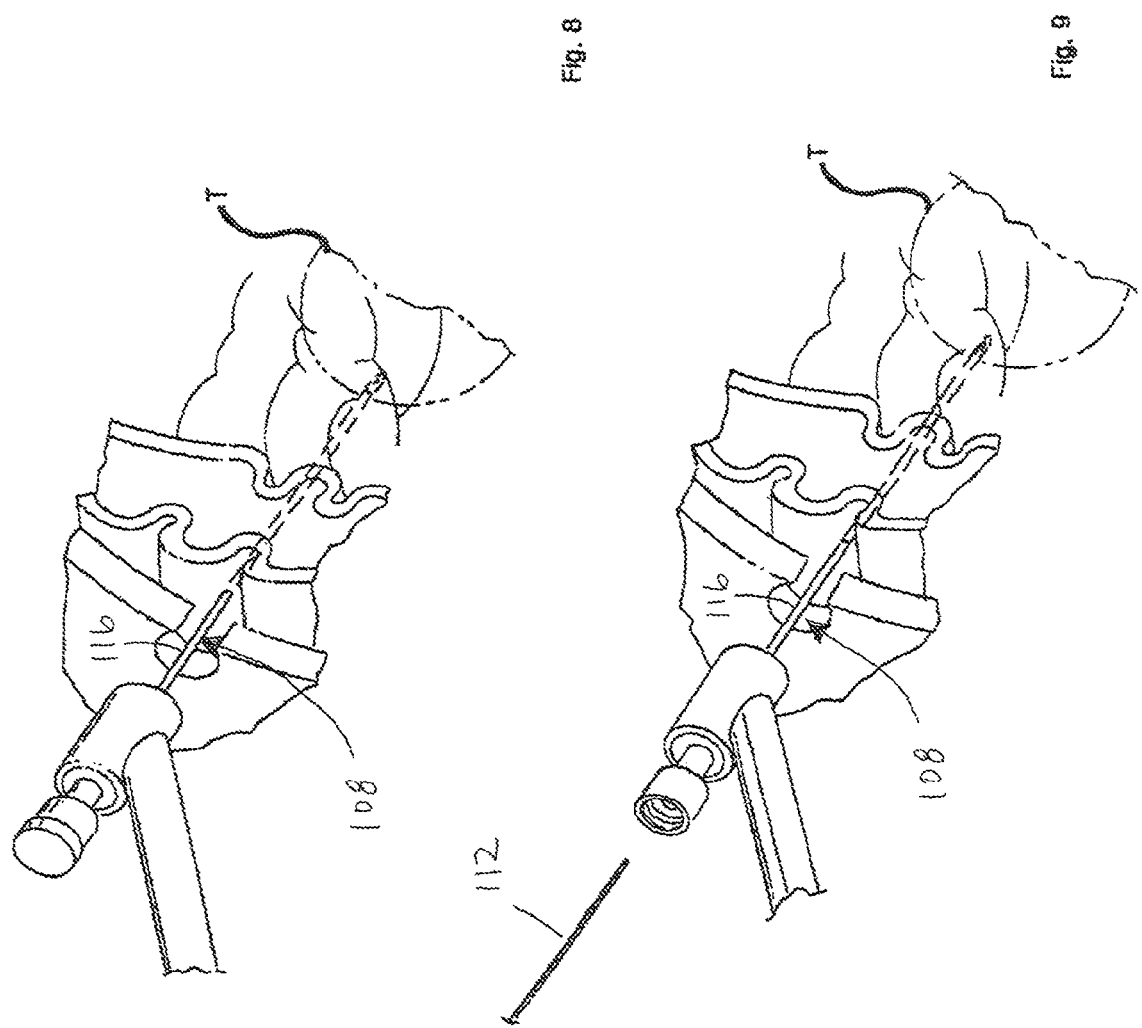

APPARATUS FOR USE IN A SURGICAL PROCEDURE

CROSS-REFERENCE TO RELATED APPLICATIONS

This application is a Continuation Application of U.S. patent application Ser. No. 13/190,830 filed on Jul. 26, 2011, which is a Divisional application of U.S. patent application Ser. No. 11/081,494 filed on Mar. 17, 2005, which is a Divisional application of U.S. patent application Ser. No. 10/373,835 filed Feb. 27, 2003, now abandoned, which claims priority from U.S. Provisional Patent Application No. 60/366,530 filed Mar. 25, 2002 and U.S. Provisional Patent Application No. 60/366,529 filed Mar. 25, 2002 the entire disclosures of each of which are incorporated herein by reference.

FIELD OF THE INVENTION

The present invention relates generally to image guided surgery and more particularly relates to a kit of parts, and the individual parts of the kit, for use in navigation during a surgical procedure.

BACKGROUND

Over one million CT-guided biopsies are performed per year in the US. There are two million ultrasound-guided biopsies a year. Many of these ultrasound biopsies are performed because computerized tomography ("CT") is not available. Ultrasound is also traditionally faster than CT, as there is the availability of substantially real time imaging. Traditionally, CT required the acquisition of an image, the passage of a needle, the acquisition of another image and the repositioning of the needle to be checked by acquisition of another image. With this process a biopsy could take hours and it was hard to keep track of the needle tip relative to the patient and know if it was necessary to angle up or down to get to the target.

The recent availability of CT fluoroscopy has radically changed management of patients. With CT fluoroscopy, cross sectional images of the body are obtained which are refreshed up to thirteen times a second. Further increases in the refresh rate are believed by the inventors to be a reasonable expectation. With some CT scanners three slices can be presented simultaneously, all being refreshed thirteen times a second. This can create a substantially flicker-free image of a needle or device being passed into the patient. This has the potential to increase speed, accuracy and ability to safely deliver needles to sensitive or delicate structures and avoid large blood vessels.

However, there are drawbacks and limitations to CT fluoroscopy. These mainly relate to issues of infection due to the procedure and radiation safety for the physician. For example, during the passage of the needle by the physician's hands into the patient under substantially real time x-ray guidance, the physician's hand is in the x-ray beam. This can result in an accumulation of excessive radiation dose to the physician's hand. The physician may perform the procedure repeatedly during his career or even during a single day and this cumulative dose becomes an issue of personal radiation safety.

Furthermore, current biopsy needles are composed of metal (e.g., stainless steel that generates significant artifacts when used with x-ray detectors of CT quality. These artifacts are related to the density of the metals used in these needles. These artifacts are called beam-hardening artifacts. These artifacts can obscure the intended target or obscure an important structure and possibly make it possible for inadvertent injury of the target. Accordingly, current biopsy needles are not generally suitable for CT image guided surgical procedures.

A further disadvantage of the prior art is that needles that are currently used for biopsies typically have the stylet attached to the trocar loosely, yet such a loose attachment can present certain hazards when using such a needle under CT imaging.

A further disadvantage of the prior art is that, since CT machines are typically used for simple capturing of images, they are typically non-sterile, and therefore, under CT image guidance procedures, elaborate sterilization can be necessary to reduce risk of patient infection. Simplified sterilization techniques are therefore desirable.

SUMMARY OF THE INVENTION

It is therefore an object of the invention to provide a kit of parts for image guided surgical procedures that obviates or mitigates at least one of the above-identified disadvantages of the prior art. In an aspect of the invention there is provided a sterile needle holder that allows the transmission of force from the physician's hand to the needle so that the needle can be guided into the patient without requiring the physician to have his hand in the x-ray beam during the procedure. It is presently preferred that the needle holder be made from materials such that artifacts are not generated (or artifacts are desirably reduced) that would obscure the target. (i.e. radio lucent).

It is therefore desirable to provide needles of decreased density. The unit of density used for CT is the Hounsfield unit after the inventor of CT, Sir Godfrey Newbold Hounsfield. Hounsfield units quantify the radiopacity (i.e., radiodensity) of a material —that is, the extent to which the material impedes the passage of radiation such as the x-rays used in CT. The radiopacity of a material under CT scanning, in Hounsfield units, is generally proportional to the physical densisty of the material (see Kim S, Lee GH, Lee S, Park SH, Pyo HB, Chos JS, "Body fat measurement in computed tomography image", Biomed Sci Instrum. 1999; 35: pages 303-308. A Hounsfield unit of zero is attributed to the density of water on CT, bone is higher in density than water, fat is lower in density than water. Fat therefore has a negative Hounsfield number. According to an aspect of the invention there is provided needles that are composed of metals or composites that are visible on CT but have a reduced likelihood of showing artifacts under CT. Needles are composed of two parts, an outer trocar and an inner stylet. Either one or the other or both can be made of diminished Hounsfield unit density material. It can be thus desirable to construct a stylet made of carbon fiber or plastic. Aluminium or Initinol or Inconel$^{198}$, are metals that are MRI compatible and may be valuable for CT purposes while at the same time being useful for MRI.

In another aspect of the invention there is provided a biopsy needle wherein the stylet is attached to the trocar via a locking means or attachment means, such as a Luer Lock™ or a simple screw system. The locking biopsy needle is thus used under CT image guidance, advanced using the needle holder. The locking needle thus can be unlocked at the desired time and reduce the likelihood of trauma or injury to the patient during navigation under CT image guidance.

In another aspect of the invention there is provided a drape that reduces contamination of the operator's hand against the side of the CT scanner. For conventional angiography, a sterilized plastic bag with an elasticated top is placed around the image intensifier and used like a sack. In a CT machine, there is provided a donut-shaped configuration and the patient passes through the central hole of the donut. Preferably, such a drape is disposable, but re-sterilizable drapes are also within the scope of the invention. It is presently preferred that the drape would be like a basketball hoop. In this particular implementation of this aspect of the invention, the basketball-hoop like drape is attachable to the open ends of the CT scanner by any suitable attachment means, such as either or a combination of a) adhesive, b) preplaced hoops affixed to the CT scanner and whereby such hoops would attach by an elasticated band to the drape; c) the drape could be made from a metal that is foldable and therefore transportable, though when released from its package would have a radial force such that it would affix the drape to either side of the CT scanner. Such a material could be Nitinol, from Nitrol Devices and Components, 47533 Westinghouse Drive, Fremont, Calif. 94539.

In another aspect of the invention there is provided a kit for use in CT guided image fluoroscopy, comprising: (1) a needle holder for keeping the operator's hand out of the beam; (2) a needle of diminished beam hardening artifact inducing potential; (3) a lock to fix the stylet with regard to the trocar in an appropriate position; and (4) a drape to protect the operator's hand from contamination.

In another aspect of the invention there is provided a kit of parts for use in an image guided surgical procedure using a substantially real time imaging machine comprising: a needle holder having a grasping means and a handle depending therefrom, the handle being configured such that the grasping means can be exposed to the imaging beam and an operator's hand can be distal from the imaging beam in relation to the grasping means; a needle attachable to the grasping means and having a rigidity to travel through mammalian tissue to a target area and having a radioopacity that substantially preserves an appearance of the needle when the needle is viewed on a display of the real time imaging machine; and a sleeve for attachment to the real time imaging machine that provides a substantially sterile operating environment for using the needle when attached to the machine.

In a particular implementation of the foregoing aspect, a locking mechanism is associated with at least one of the grasping means and the needle for releasably locking the needle to the needle holder.

In another aspect of the invention there is provided a surgical instrument for use in an image guided surgical procedure using a substantially real time imaging machine comprising: a needle holder having a grasping means and a handle depending therefrom, the handle being configured such that the grasping means can be exposed to the imaging beam and an operator's hand can be kept a distance away from the imaging beam; and a needle attachable to the grasping means and having a rigidity to travel through mammalian tissue to a target area and having a radioopacity that substantially preserves an appearance of the needle when the needle is viewed on a display of the real time imaging machine.

In a particular implementation of the foregoing aspect, the needle is a trocar comprising a cannula and a stylet receivable within the cannula.

In a particular implementation of the foregoing aspect, a locking mechanism is associated with at least one of the grasping means and the needle for releasably locking the needle to the needle holder.

In another aspect of the invention there is provided a sterile drape for attachment to a real time imaging machine comprising: a sheet of material for providing a substantially sterile barrier between the imaging machine and a patient; and an attachment means for affixing the drape to the imaging machine.

In a particular implementation of the foregoing aspect, the sheet of material is plastic and substantially tubular.

In a particular implementation of the foregoing aspect, the imaging machine has a pair of annular lips that flare outwardly from a respective opening of the machine and wherein the attachment means comprises an annular shaped elastic integral with each open respective ends of the sheet, each of the elastics for grasping a respective lip.

In a particular implementation of the foregoing aspect, the drape is umbrella-like, in that the material is plastic and the attachment means is a series of series of rods integrally affixed to the plastic, the rods made from a springed material such that the sleeve has a first position wherein the sleeve is collapsed and a second position wherein the sleeve is outwardly springed.

In a particular implementation of the foregoing aspect, the material is nitinol and the attachment means is achieved through configuring the nitinol to be outwardly springed.

In a particular implementation of the foregoing aspect, the attachment means is selected from the group consisting of velcro, ties, or snaps.

In another aspect of the invention there is provided an imaging machine comprising a channel for receiving a patient and exposing the patient to a substantially real time imaging beam. The machine also includes an attachment means for affixing a sterile drape to the channel, such that when the sterile drape is attached thereto a substantially sterile barrier between the channel and the patient is provided, thereby providing a substantially sterile environment for the patient.

In a particular implementation of the foregoing aspect, the attachment means is comprised of a pair of annular lips flanged so as to provide a secure attachment to a pair of annular elastized openings of a sterile sleeve.

In a particular implementation of the foregoing aspect, the beam is selected from the group consisting of CT, MRI, and X-Ray.

In a particular implementation of the foregoing aspect, a refresh rate of the real-time imaging beam is greater than, or equal to, about thirteen frames per second. The rate can be greater than about thirty frames per second. The rate can also be greater than about fifty frames per second. In other implementations, however, it is contemplated that the refresh rate can be as low as about one frame per second, depending on the actual procedure being performed and/or the imaging device being used.

BRIEF DESCRIPTIONS OF THE DRAWINGS

Embodiments of the invention will now be discussed, by way of example only, with reference to the attached Figures, in which:

FIG. 7 is an assembled view of the needle apparatus of FIG. 6 just prior to use;

FIG. 8 shows the needle apparatus of FIG. 7 being inserted into a target area of a patient;

FIG. 9 shows the stylet of the needle holder of FIG. 7 being removed; and,

DETAILED DESCRIPTION OF THE EMBODIMENTS

Figure 1:
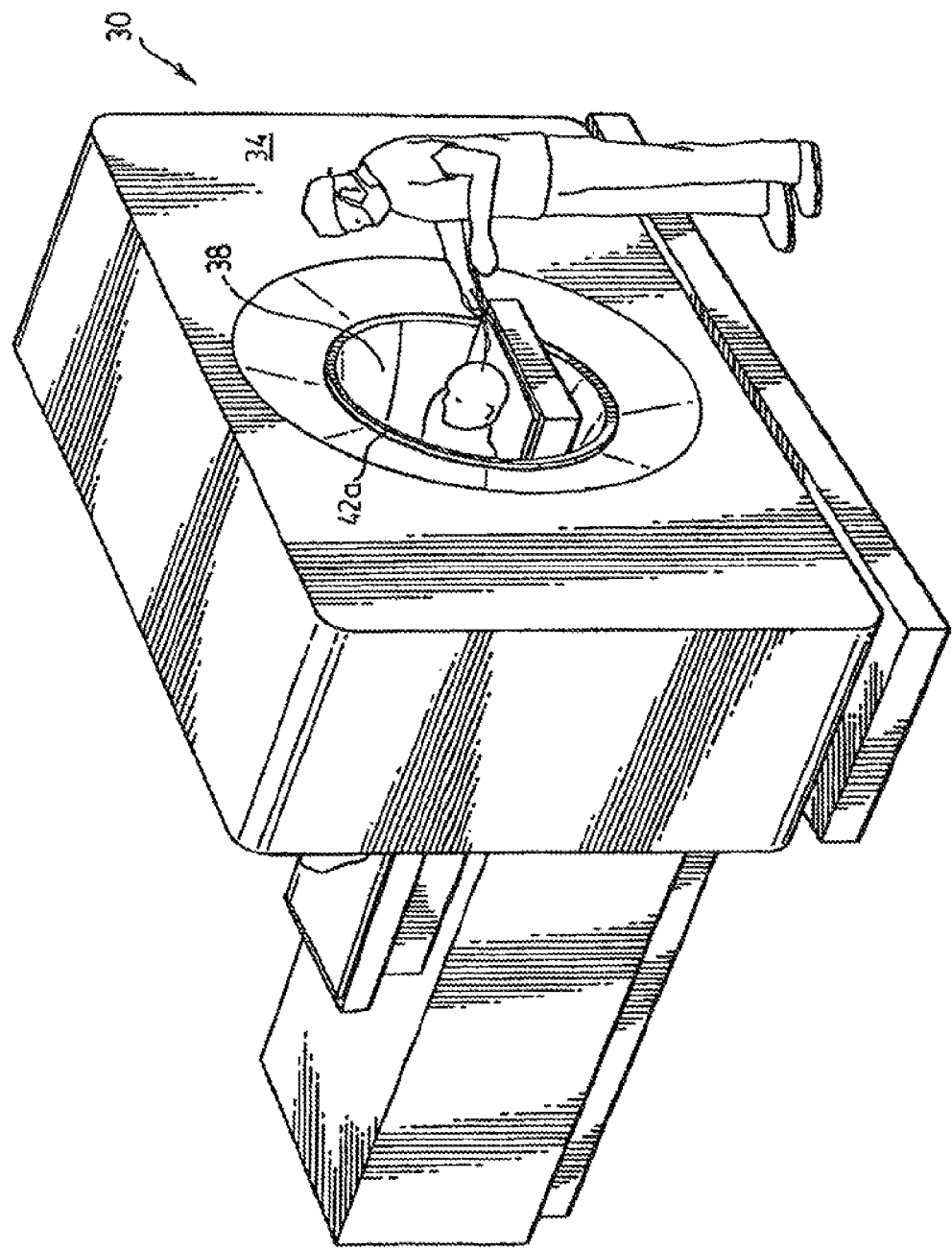
FIG. 1 is a front perspective view of a CT machine in accordance with an embodiment of the invention.
Figure 2:
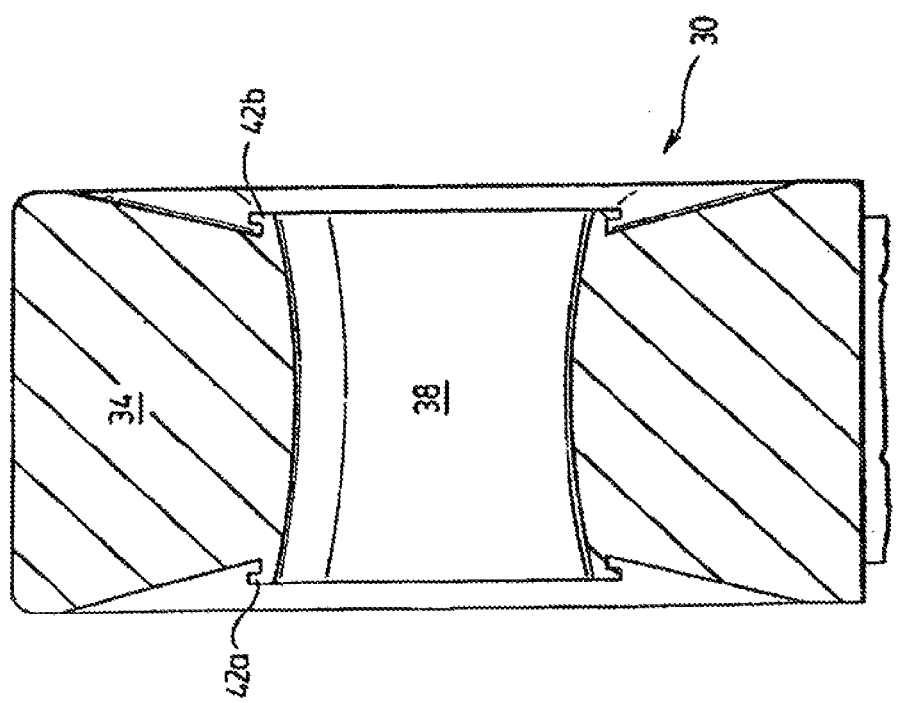
FIG. 2 is a side sectional view of the CT machine of FIG. 1.

Referring now to FIGS. 1 and 2, a computerized tomography ("CT") imaging machine in accordance with an embodiment of the invention is indicated generally at 30. CT Machine 30 is composed of a chassis 34 and a channel 38 through which a patient is received in order to capture the desired images of the patient and/or perform any desired procedures. A presently preferred CT machine for use in the present embodiment is an imaging machine capable of generating substantially real time images. In order to generate images in substantially real time, the imaging machine can generate images at a rate of about fifty frames per second or greater. However, substantially real time images suitable for the present embodiment can also be generated by machines capable of generating images at a rate of about thirty frames per second or greater. However, substantially real time images suitable for the present embodiment can also be generated by a machine capable of generating images at a rate of about thirteen frames per second or greater. A presently preferred substantially real time imaging machine is the Toshiba Aquillon, a CT machine, which generates images at a rate of about thirteen frames per second for use in performing procedures under CT image guidance.

As will be understood by those of skill in the art, chassis 34 in FIGS. 1 and 2 is a simplified representation used for purposes of explaining the present embodiment, and thus also contain the requisite imaging beam technology to provide the desired CT imaging functionality.

Thus, machine 30 is further characterized by a pair of annular lips 42a and 42b, (or other attachment means) that flare outwardly from a respective opening of channel 38 and away from chassis 34. Each lip 42 attaches to chassis 34 at the periphery of channel 38, where channel 38 meets chassis 34 at the ends of machine 30. Further details on machine 30 and lips 42 and its use will be discussed in greater detail later below.

Figure 3:
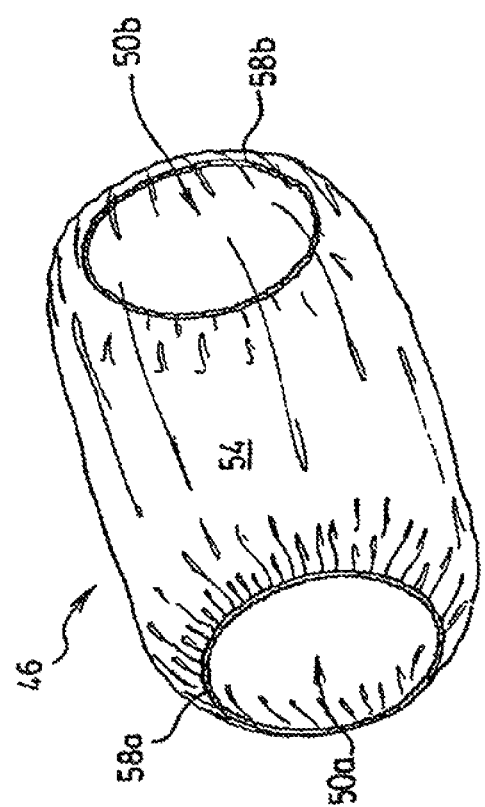
FIG. 3 is a perspective view of a drape for use with the machine shown in FIG. 1 in accordance with another embodiment of the invention.

Referring now to FIG. 3, a sterile sleeve is indicated generally at 46, in accordance with another embodiment of the invention. In the present embodiment, sleeve 46 is comprised of a substantially tubular sterilized plastic sheet (or other suitably flexible material that will not interfere with the imaging beam of machine 30). While not shown in the Figures, sleeve 46 is thus typically pre-sterilized and then folded for storage (all while maintaining sterility) within a sterile packaging. The sterile packaging is thus not opened until sleeve 46 is put into use, and only then opened under acceptable and/or desirable sterile conditions.

Sleeve 46 is thus further characterized by a pair of annular openings 50a and 50b interconnected by a continuous plastic sheet 54. Each opening 50a and 50b is further characterized by an elastic 58a and 58b encased within the sleeve at the periphery of its respective opening 50a and 50b.

Referring again to FIGS. 1 and 2, in conjunction with FIG. 3, the length of sheet 54 between each opening 50a and 50b is substantially the same as the length between each lip 42a and 42b. Further, the diameter of sheet 54 typically will substantially match the variation in the diameter of channel 38 along its length, the diameter of sheet 54 being slightly smaller than the diameter of channel 38 therealong.

Figure 5:
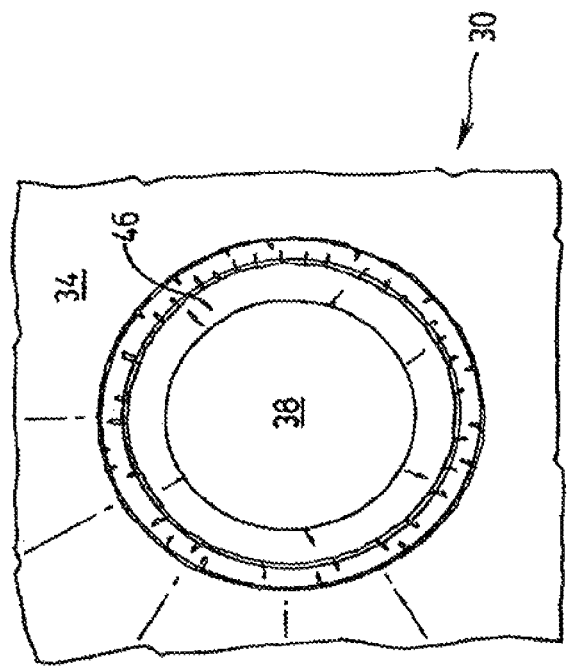
FIG. 5 is a front view the drape of FIG. 3 assembled to the machine shown in FIG. 4, in the direction of the lines V-V of FIG. 4.
Figure 4:
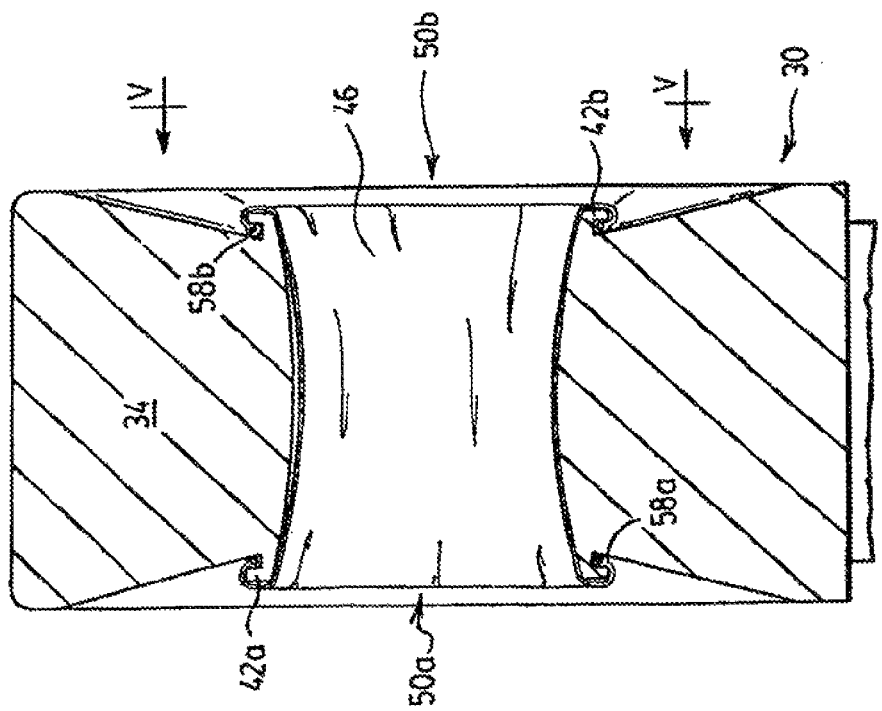
FIG. 4 is the side sectional view of FIG. 2 but with the drape of FIG. 3 assembled to the machine.

Referring now to FIGS. 4 and 5, sleeve 46 is shown assembled to machine 30. In order to perform such assembly, the packaging containing sleeve 46 is opened, in sterile conditions, and sleeve 46 is unfolded, just prior to the use of machine 30 for capturing images and/or for performing a procedure under image guidance. Accordingly, to assemble sleeve 46 with machine 30, elastic 58a is first stretched and passed over lip 42a, thereby securing the sleeve at opening 50a to lip 42a, and widening opening 50a so that it is substantially the same size as the opening of channel 38. Next, the remainder of sleeve 46 including sheet 54 and opening 50b are passed through channel 38 towards and through the opening of channel 38 opposite from lip 42a. Elastic 58b is then stretched so that the sheet at opening 50b extends over lip 42b, thereby securing the sleeve at the opening 50b to lip 42b, thereby completing the assembly of sleeve 46 to machine 30, as seen in FIGS. 4 and 5. Accordingly, CT machine 30 can now be used in a sterile manner. When the use of CT machine 30 is completed, sleeve 46 can simply be disassembled therefrom by substantially reversing the above-described assembly steps, and then disposed of, or re-sterilized, as desired and/or appropriate to provide patient safety.

It will now be understood that sleeve 46 and machine 30 are complementary to each other, and thus, the various components and dimensions of sleeve 46 are chosen to correspond with the complementary parts on machine 30. Thus, for example, elastics 58 are chosen to have a material and elasticity such that assembly of the sleeve at an opening 50 to a corresponding lip 42 can be performed with relative ease. In other words, the elasticity is chosen so that the person performing the assembly will not have to apply undue force to actually expand elastic 58 and fit it around lip 42. By the same token the elasticity of elastic 58 is sufficiently strong to ensure a reliable attachment of the sleeve at opening 50 to the corresponding lip 42 during the capturing of images or performance of a surgical procedure under image guidance. Furthermore the diameter of sheet 54 is chosen so as to not substantially reduce the diameter of channel 38 after assembly. The material of sheet 54 is also chosen so as to not interfere with the imaging beam generated by machine 30.

It should also now be understood that sheet 54 can be constructed in different shapes to complement different types and shapes of imaging machines that are capable of providing substantially real time images and thereby could benefit from the sterile sleeve of the present invention. In particular, sheet 54 may only have one opening 50, depending on the type of imaging machine with which it is used. By the same token, it will be understood that any variety of mechanical substitutes to the cooperating lips 42 and elastics 58 can be provided, and that such substitutes are within the scope of the invention. Thus, in general, any cooperating attachment means between sleeve 46 and machine 30 can be provided, and such varied cooperating attachment means are within the scope of the invention. For example, hooks and loops, velcro, ties, and/or snap-buttons or the like can be used as cooperating attachment means. By the same token, it is to be understood that lip 42 (or any suitable mechanical equivalent) can be retrofitted onto existing CT machines, or built directly thereto, as desired.

Furthermore, the location of the cooperating attachment means on machine 30 and sleeve 46 need not necessarily be limited to the respective distal ends of machine 30 and sleeve 46, but need only result in the ability to assemble sleeve 46 to machine 30 while leaving a suitable and appropriately substantially sterile passageway within channel 38 for receiving a patient. In another variation of the foregoing, sleeve 46 could be made from a rigid material, or an outwardly springed material, to thereby obviate the need for lip 42 or any means of attachment actually connected to machine 30.

Figure 6:
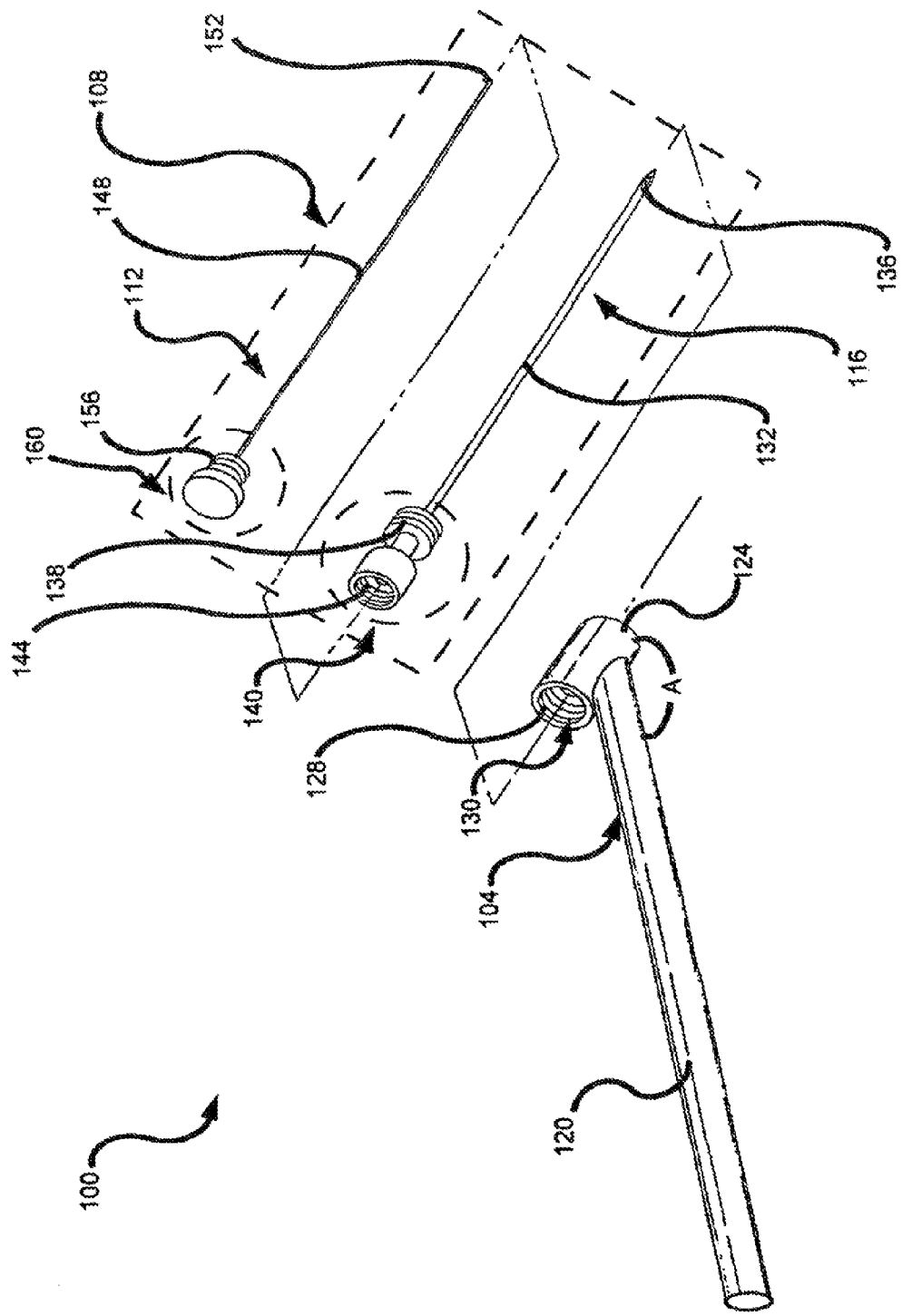
FIG. 6 is an exploded perspective view of a needle apparatus in accordance with an embodiment of the invention.

Referring now to FIGS. 6-8, a needle apparatus for use under substantially real time image guidance is indicated generally at 100 and is in accordance with another embodiment of the invention. Needle apparatus 100 comprises a needle holder 104 and a trocar 108, which itself is comprised of a stylet 112 and a cannula 116.

Needle holder 104 is typically made of a plastic or other material that does not appear under CT image guidance (or under the imaging beam of the particular imaging machine being used). Holder 104 is comprised of a handle portion 120 and a grasping portion 124. In a present embodiment, handle portion 120 depends from grasping portion at an angle "A" greater than about ninety degrees, however, handle portion 120 can actually depend from grasping portion 124 at ninety-degrees or any other desired angle, depending on the procedure being performed, and the preferences of the surgeon or other medical professional performing the procedure. In a present embodiment, handle portion 120 is substantially cylindrical, but can be any desired shape and length, again depending on the preferences and/or needs of the procedure and/or surgeon. Grasping portion 124 is also substantially cylindrical, but is further characterized by a hollow channel 130 through which cannula 116 can be passed, and it is presently preferred its hollow channel 130 is of a slightly larger diameter than cannula 116 to securely hold cannula 116 within grasping portion 124. In a present embodiment, grasping portion 124 includes a set of interior threads 128 located on the portion of grasping portion 124 located nearest handle portion 120.

Cannula 116 is comprised of a hollow shaft 132 with a tip 136. Tip 136 has a desired shape for piercing the target area of the patient in a desired manner. It is presently preferred that shaft 132 be made from a material that is hard enough to pierce the patient's target area, yet also made from a material that presents reduced and/or minimal artifacts when shaft 132 is viewed under a CT imaging beam using a CT machine, (such as machine 30 shown in FIG. 1), such that appearance of shaft 132 is substantially preserved when viewed under such an imaging beam.

Cannula 116 is also characterized by a set of exterior threads 138 towards the proximal end 140 of cannula 116 opposite from tip 136. Exterior threads 138 are thus complementary to interior threads 128 of grasping portion 124, such that trocar 108 can be releasably secured to grasping portion 124. Cannula 116 is also characterized by a set of interior threads 144 at the proximal end 140 of cannula 116, proximal end 140 also being made from a material that presents reduced and/or minimal artifacts when viewed under a CT imaging beam such that appearance of proximal end 140 is substantially preserved when viewed under such an imaging beam.

Stylet 112 is comprised of a needle having a solid shaft 148 including a point 152 at its distal end. Point 152 is complementary to tip 136, and the length of shaft 148 is substantially the same length as shaft 132, such that when stylet 112 is inserted within and assembled to cannula 116, point 152 and tip 136 form a contiguous shape. Solid shaft 148 is preferably made from substantially the same material as shaft 132, such that shaft 148 is hard enough and/or rigid to pierce a target area T within the patient, yet also made from a material that presents reduced and/or minimal artifacts and/or no artifacts when shaft 132 is viewed under a CT imaging beam using a CT machine, (such as machine 30 shown in FIG. 1), such that appearance of stylet 112 is substantially preserved when viewed under such an imaging beam. Suitable materials can include, for example, certain carbon fibres, inconel etc. Other materials will now occur to those of skill in art.

Stylet 112 is also characterized by a set of exterior threads 156 at the proximal end 160 of stylet 112 opposite from point 152. Proximal end 160 is also made from a material that presents reduced and/or minimal artifacts when viewed under a CT imaging beam, again, such that appearance of proximal end 160 is substantially preserved when viewed under such an imaging beam. Exterior threads 156 are thus complementary to interior threads 144, such that stylet 112 can be releasably secured to cannula 116.

As discussed above, the materials from which one or both of cannula 116 and stylet 112 are manufactured have lower radiopacity (that is, lower Hounsfield values) as compared to conventional needle components (which are generally stainless steel) in order to reduce the incidence of artifacts under CT imaging. The material from which one or both of cannula 116 and stylet 112 are manufactured is selected from the group including aluminum, carbon fiber, plastic, nitinol and Inconel. Known examples of plastics include nylon, Poly (methyl methacrylate) (PMMA), also known as Lucite or acrylic), Polyethe ether ketone (PEEK), polycarbonate and polyethylene.

Table 1 lists Hounsfield values for various materials (see van der Glas M. "Principles of Computerized Tomographic Imaging", 2000; Summerscales J, "Non-destructive testing of fibre- reinforced plastics composites, Volume 2"; Elsevier Science Publishers Ltd, 1990; page 208; and Chen-Yuan C. ei al., "Beam Hardening Correction for Computed Tomography Images Using a Postreconstruction Method and Equivalent Tissue Concept", Journal of Digital Imaging, Vol. 14, No. 2, 2001, pp. 54-61):

TABLE 1

| Material | Hounsfield Value |
| --- | --- |
| Air | −1000 |
| Lung | −500 to −200 |
| Fat | −200 to −50 |
| Water | 0 |
| Blood | 25 |
| Muscle | 25 to 40 |
| Nylon | 80 |
| Polycarbonate | 85 |
| Polyethylene | 90 |
| PMMA (Lucite/acrylic) | 110 |
| Carbon | 580 |
| Bone | 1000 |

TABLE 1-continued

| Material | Hounsfield Value |
|---|---|
| Aluminum | 1900 |
| Iron | 24000 |

As seen in Table 1, materials such as plastics, carbon and aluminum, from which one or both of cannula 116 and stylet 112 can been made, have lower Hounsfield values than other metals such as iron, and also present reduced artifacts under CT imaging. Aluminum, PMMA and carbon have lower physical densities than iron and stainless steel.

Use of apparatus 100 is represented in FIG. I and FIGS. 7-9. In use, assembled needle apparatus 100 as shown in FIG. 7 is grasped by a surgeon by handle portion 120, towards or at the end of handle portion 120 opposite from grasping portion 124. Thusly grasped, trocar 108 and grasping portion 124 are then placed within the imaging beam (e.g. the beam within channel 38 of machine 30 in FIG. 1) when the machine is "on", the surgeon being careful to keep his or her hand out of the imaging beam. Trocar 108 is thus viewed on the display of machine 30, and guided to the target area of the patient also located within channel 38. Trocar 108 can thus be used in any desired procedure under such image guidance while keeping the surgeon's hand from harm's way. For example, as seen in FIG. 8, trocar 108 is shown piercing through brain tissue towards a target area T inside the patient. As seen in FIG. 9, stylet 112 is removed from cannula 116 by first disengaging threads 156 from threads 144, thereby leaving a hollow channel between the exterior of the patient and the target area T. This hollow channel can then be used in any desired manner, such as to drain excess cerebral spinal fluid, to treat a clot and/or to insert a catheter according to the shunt implantation method taught in the copending U.S. Formal patent application Ser. No. 10/361,692 entitled "Method, Device and System for Implanting a Shunt" filed on Feb. 11, 2003 (U.S. publication no. 2003/0181807 A1).

It is to be understood that various combinations, subsets and equivalents can be employed in the foregoing description of apparatus 100. For example, any one or more of pairs of threads 156 and 144, or 138 and 128, can be reversed and/or substituted for a Luer-Lock™ system. Furthermore, any one of pairs of threads 156 and 144, or 138 and 128 could be replaced by a clamping mechanism. For example, grasping portion 124 could be replaced with a mechanical clamp that surrounds proximal end 140 of cannula 116.

Figure 10:
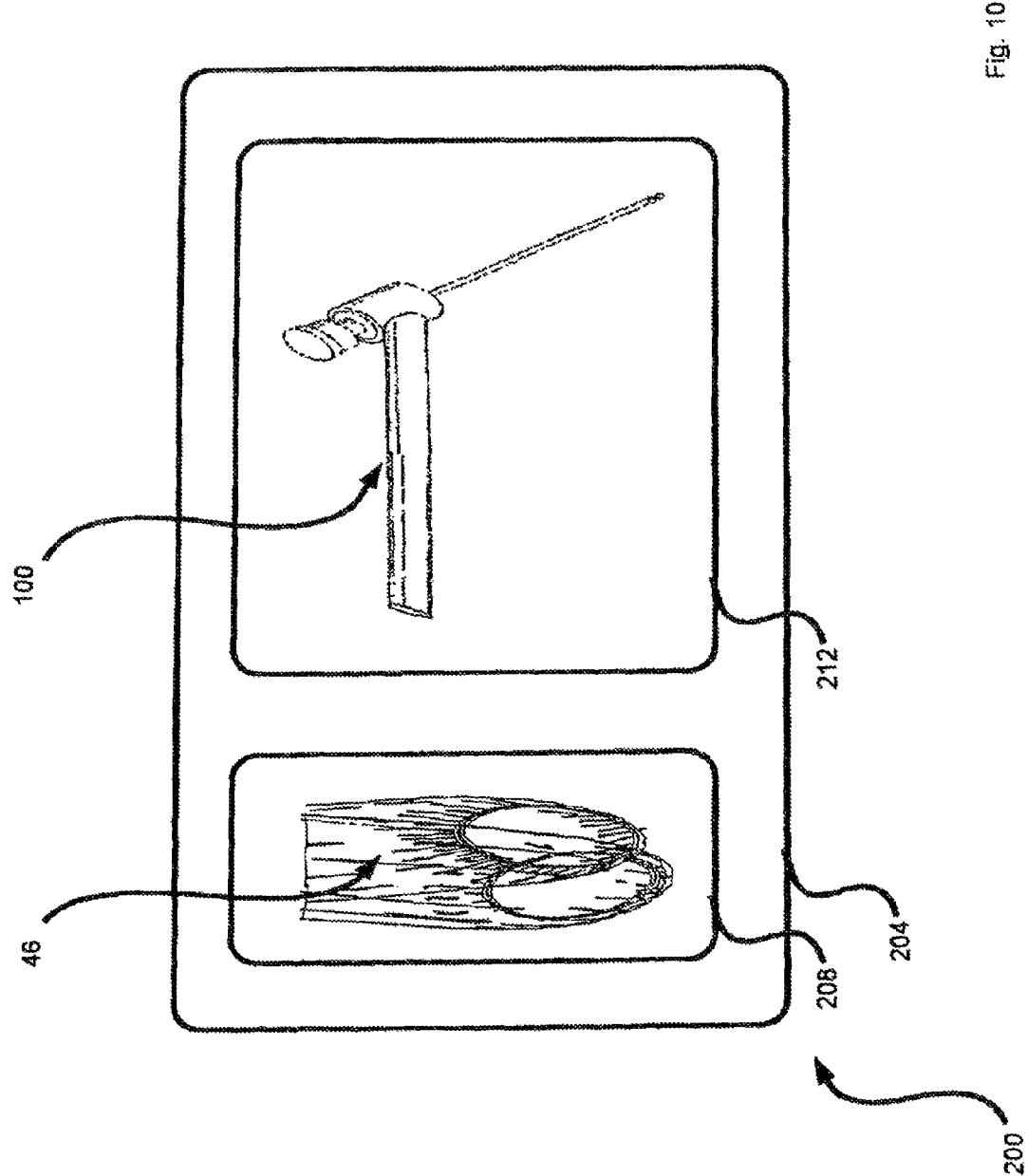
FIG. 10 is a kit of parts including the drape of FIG. 3 and the needle holder of FIG. 6 in accordance with another embodiment of the invention.

Referring now to FIG. 10, a kit for performing image guided surgical procedures is indicated generally at 200. Kit 200 comprises a sterile package 204 which includes two sterile compartments 208 and 212. Compartment 208 houses sleeve 46 and compartment 212 houses apparatus 100. Kit 200 can then be distributed to hospitals and clinics. Prior to performing a surgical procedure, compartment 208 can be opened and sleeve 46 applied to the corresponding CT machine. When the patient is prepped, compartment 208 can be opened and the apparatus 100 therein used as previously described. Kit 200 can include such other components as desired to perform a particular procedure under substantially real time image guidance.

While only specific combinations of the various features and components of the present invention have been discussed herein, it will be apparent to those of skill in the art that desired subsets of the disclosed features and components and/or alternative combinations of these features and components can be utilized, as desired. For example, while the embodiments discussed herein refer to CT machines, it is to be understood that the teachings herein can be applied to any type of imaging machine capable of generating substantially real time images, such as machines based computerized tomography ("CT"), magnetic resonance ("MR"), or X-Ray.

The above-described embodiments of the invention are intended to be examples of the present invention and alterations and modifications may be effected thereto, by those of skill in the art, without departing from the scope of the invention which is defined solely by the claims appended hereto.

The invention claimed is:

1. A biopsy needle for use in biopsies guided by a computed tomography (CT) imaging apparatus, comprising:
   a biopsy needle stylet having a solid shaft and being made of a first material selected from carbon fibre or plastic such that an appearance of the solid shaft generated by the CT imaging apparatus presents reduced imaging artifacts;
   a biopsy needle cannula having a hollow shaft configured to receive the solid shaft of the stylet, a proximal end and a distal end remote from the proximal end, the cannula being made of a second material selected from the group consisting of stainless steel, aluminum, nitinol, and Inconel, and the distal end being configured to pierce tissues of a patient;
   wherein the solid shaft of the stylet is positioned wholly inside the cannula and has a proximal end and an opposing distal end, the proximal end of the stylet being configured to fix the stylet to the cannula and the opposing distal end of the stylet being contiguous with the distal end of the cannula, and wherein the distal end of the cannula is effective to pierce tissues of a patient.

2. The needle of claim 1 wherein the second material is not stainless steel and has a radiopacity lower than the radiopacity of stainless steel, such that an appearance of the solid shaft generated by the CT imaging apparatus presents reduced imaging artifacts.

3. The needle of claim 1 wherein the first material has a Hounsfield value of less than 1900.

4. The needle of claim 1 wherein the first material is plastic.

5. The needle of claim 4 wherein the first material is selected from the group consisting of nylon, polycarbonate, acrylic, and polyether ether ketone (PEEK).

6. The needle of claim 1 wherein the second material is stainless steel.

7. The needle of claim 1 wherein the second material is aluminum.

8. The needle of claim 1 wherein the solid shaft is made entirely of the first material.

9. The needle of claim 1 wherein the proximal end of the solid shaft and the proximal end of the hollow shaft have complementary locking mechanisms.

10. The needle of claim 9 wherein the complementary locking mechanisms are complementary threads.

11. The needle of claim 9 wherein the complementary locking mechanisms are complementary Luer lock fittings.

12. The needle of claim 5, wherein the first material is nylon.

* * * * *